United States Patent
Fuchs et al.

(12) 
(10) Patent No.: US 6,197,784 B1
(45) Date of Patent: Mar. 6, 2001

(54) PROCESS FOR CONTROLLING AND DESTROYING PATHOGENIC SMALL CREATURES, IN PARTICULAR INSECTS AND WORMS

(75) Inventors: Rainer Fuchs, Mömbris/Hohl; Michael Huss, Eschborn, both of (DE)

(73) Assignee: Degussa-Huls AG, Frankfurt am Main (DE)

( * ) Notice: Subject to any disclaimer, the term of this patent is extended or adjusted under 35 U.S.C. 154(b) by 0 days.

(21) Appl. No.: 09/274,906

(22) Filed: Mar. 23, 1999

(30) Foreign Application Priority Data

Mar. 23, 1998 (DE) .............................. 198 12 590

(51) Int. Cl.$^7$ .................................... A01N 37/00
(52) U.S. Cl. .......................... 514/307; 514/557
(58) Field of Search .............................. 514/557; 504/307

(56) References Cited

U.S. PATENT DOCUMENTS 4,966,706   10/1990   Gregor .................................. 210/609

FOREIGN PATENT DOCUMENTS

WO 96/18301   6/1996   (WO).
WO 98/25456   6/1998   (WO).

OTHER PUBLICATIONS

Gill et al, Battling thrips: Five pesticides put to the test, Grower Talks, vol. 62, No. 8, pp. 46–48, 1998.*

Anon, Lice control from Mackie, Fish Farm. Int., vol. 25, No. 2, p. 51, 1998.*

Chemical Abstracts, vol. 114, No. 15, Abstract No. 138069, XP002107262 (15 Apr. 1991).

Database CABA, Avramova et al., vol. 22, No. 1, pp. 53–56, "Study of the effect of some disinfectants on helminth ova", STN–Accession No. 86:12010, XP002107264.

Database AQUASCI, vol. 25, No. 2, p. 51, "Lice control from Mackie", STN–accession No. 1998; XP002107265.

Database CABA, Gill, vol. 62, No. 8, pp. 46–48, "Battling thrips: five pesticides put to the test", STN–accession No. 1999;29052, XP002107266.

Chemical Abstracts, vol. 77, No. 13, Abstract No. 83962, XP002107263, Radvan, "Effect of aliphatic peracids on the eggs of Ascaris suum in vitro" (25 Sep. 1972.

Database CABA, Gulden et al., vol. 22, No.2, pp. 225–226, "The effect of peracetic acid s a disinfectant on worm eggs", STN–accession No. 73:67085, XP002107267.

\* cited by examiner

*Primary Examiner*—S. Mark Clardy
*Assistant Examiner*—Alton Pryor
(74) *Attorney, Agent, or Firm*—Pillsbury Madison & Sutro LLP

(57) ABSTRACT

Small creatures from the group of insects and worms which are pathogenic to humans, animals and plants can be controlled effectively by applying or introducing an aqueous percarboxylic acid solution containing one or more percarboxylic acids with 1 to 6 carbon atoms to surfaces and/or into water. A solution which contains peracetic acid and/or performic acid is preferably used. In the case of insects, the larvae of these are controlled in water using an application concentration of 1 to 5000 ppm of percarboxylic acid.

23 Claims, No Drawings

PROCESS FOR CONTROLLING AND DESTROYING PATHOGENIC SMALL CREATURES, IN PARTICULAR INSECTS AND WORMS

FIELD OF THE INVENTION

The invention relates to a process for controlling and destroying pathogenic small creatures, in particular insects and worms.

BACKGROUND OF THE INVENTION

For as long as anyone can remember, humans and animals and also plants have been plagued or harmed by a variety of pathogenic small creatures from the groups of insects and worms. Mosquitoes, such as malaria-carrying anopheles mosquitoes, and the larvae of schistosoma (trematodes) which cause bilharziasis may be mentioned by way of example.

There has been no lack of effort to eradicate malaria. Thus, the insecticide DDT was previously sprayed in large amounts in order to control the mosquitoes. However, the good effects had to be balanced against damage to the ecological equilibrium and the use of DDT has now been banned.

The use of chlorine-releasing agents, such as sodium hypochlorite, has also been tried. Again, this agent did not gain general acceptance because it is difficult to handle and, when used in inland waters, it inevitably leads to undesirable salt production and the formation of undesirable chlorinated organic compounds. In tropical and sub-tropical countries, attempts have also been made to lower the surface tension of waters by using surfactants in order to prevent the larvae remaining below the surface of the water. The disadvantages of this technique, these being responsible for the limited use of this method, are that some of the mosquitoes can escape from the range of spread of the surfactants and/or too large an amount of surfactant is required.

U.S. Pat. No. 5,393,781 discloses controlling zebra mussels in cooling circuits by using a peracetic acid solution. This document does not mention any other classes of animals which could be controlled using peracetic acid. The use of peracetic acid as a microbicide for controlling bacteria, viruses, yeasts, algae and moulds has been known for a long time.

SUMMARY OF THE INVENTION

The object of the invention is to provide a process for controlling and destroying disease-causing and/or troublesome insects which does not have the disadvantages inherent in the methods used hitherto, or exhibits them to a much smaller extent.

The object is achieved by a process for controlling and destroying small creatures from the group of insects and worms which are pathogenic to humans, animals and plants, by the application or introduction of a liquid controlling agent to surfaces and/or in waters, which is characterised in that an aqueous percarboxylic acid solution, containing one or more percarboxylic acids with 1 to 6 carbon atoms, is used as the controlling agent.

The small creatures to be controlled, wherein "controlled" is understood to mean a reduction in the population, are small creatures from the classes of insects and worms which are pathogenic to humans and animals. The process according to the invention relates in a particular manner to the control of pathogenic insects by destroying the larvae in their preferred habitat. The preferred habitat of larvae is a moist medium, in particular substantially stagnant, shallow waters such as near the banks of lakes, ponds, paddy-fields, swamps and the like. Pathogenic worms can be controlled in the same way, wherein application in shallow waters is of special importance. Examples of insects which are present in tropical and sub-tropical areas and which can be controlled according to the invention are mosquitoes, flies and bugs which transfer unicellular organisms, threadworms and viruses by stinging or on contact and may thus cause serious illnesses. Examples are, when they sting, anopheles mosquitoes that introduce plasmodia which lead to malaria; sandflies that introduce leishmania which causes kala-azar skin disease; tse-tse flies that transfer trypanosoma which initiates sleeping sickness; certain mosquitoes that transfer viruses which cause dengue fever; other mosquitoes that transfer the agent which causes yellow fever; finally the midges which are present in particular in the vicinity of paddy-fields and which cause Japanese encephalitis, should be mentioned.

Among the pathogenic worms which need to be controlled, the schistosoma (trematodes, leeches) which cause bilharziasis are of particular importance. Infection takes place through contact of humans with freshwater and brackish water in which schistosoma larvae are present. To control the larvae, it is expedient to treat shallow, stagnant waters, in particular in the vicinity of the bank, with a solution of percarboxylic acid. Tapeworms and threadworms which are pathogenic to fish and which live in water can be controlled in a similar manner.

To control larvae of, for example, worms which live in the vicinity of the surface of soil, such as hookworms which can lead to ancylostomiasis following contact with the skin, percarboxylic acid solution can be applied to the soil at an effective concentration.

An effective concentration of percarboxylic acid(s) in the medium being treated is normally in the range from 1 to 5000 ppm, in particular in the range from 10 to 500 ppm. The treatment of surfaces, such as soil or water surfaces, can be achieved by means of spraying equipment which is conventionally used for agricultural purposes, such as large spray guns or vehicles with wide booms which are provided with nozzles. For the treatment of surface layers of water, percarboxylic acid solution may also be introduced directly into the water and distributed by means of appropriate mixing devices such as pumps or ship's propellers.

The percarboxylic acids to be used, which are also called peroxycarboxylic acids, may be monoperoxy-$C_1$–$C_6$-monocarboxylic acids, monoperoxy- or diperoxy-$C_4$–$C_6$-dicarboxylic acids or monoperoxyhydroxycarboxylic acids with 2 to 6 carbon atoms and 1 or 2 hydroxyl groups. Examples are performic acid, peracetic acid, perpropionic acid, mono- and diperoxysuccinic acid, mono- and diperoxyglutaric acid, peroxylactic acid, peroxyglycolic acid and peroxytartaric acid. Peracetic acid, performic acid and solutions containing peracetic acid and performic acid are preferred.

In general, as a result of the method of preparation, the solutions contain hydrogen peroxide and the carboxylic acid(s) from which the percarboxylic acid(s) is/are derived. In addition, the solutions generally contain a mineral acid catalyst which accelerates establishment of the equilibrium. The highest peracid concentration which can be achieved during reaction of hydrogen peroxide with a carboxylic acid in the aqueous phase with a given ratio by weight of the reaction partners, is the equilibrium concentration. Accordingly solutions in or close to the equilibrium state or dilute solutions which have been obtained therefrom by diluting with water before use are used. The undiluted solutions to be used expediently contain about 0.1 to about 5 moles, in particular 0.2 to 2 moles, of percarboxylic acid per liter.

DETAILED DESCRIPTION OF THE PREFERRED EMBODIMENTS

In accordance with a preferred embodiment, a percarboxylic acid solution is used which contains, as a result of the method of preparation, orthophosphoric acid, pyrophosphoric acid and/or polyphosphoric acid of the formula $H_{n+2}P_nO_{3n+1}$, wherein n is an integer equal to or greater than 3, in particular 3 to 10. The concentration of these types of phosphoric acids is generally in the range from about 0.1 to about 3 wt. %, in particular about 0.5 to about 1 wt. %. These types of solutions preferably contain peracetic acid or performic acid or both carboxylic acids as the percarboxylic acid, wherein this combination has preferably been produced in situ prior to use, for example by mixing a peracetic acid solution and a source of formic acid, such as formic acid or a water-soluble formate, and allowing the mixture to stand for from a few minutes up to a few hours.

An advantage of this type of solution is regarded as the fact that the phosphoric acid component is more beneficial from an ecological point of view than the conventionally used sulfuric acid, when introducing the percarboxylic acid solution into the medium to be treated, such as in particular water. An advantage which is provided by any percarboxylic acid solutions which contain a combination of peracetic acid and performic acid is the increased effectiveness as compared with solutions which contain only peracetic acid as the percarboxylic acid. Solutions with the two named percarboxylic acids also demonstrate benefits as compared with any solutions which contain exclusively performic acid as the percarboxylic acid because the manufacture of performic acid, for reasons of safety and handling, is not without its problems.

In accordance with another embodiment, the percarboxylic acid solution to be used also contains one or more surfactants. Readily biodegradable surfactants are preferred, such are those already used for controlling insects. These are in particular anionic and nonionic surfactants such as, for example, sugar surfactants, alkanol sulfates or ethoxylated alcohols. The surfactant concentration in the percarboxylic acid solution to be sprayed out or to be introduced directly into waters is selected in such a way that an effect is produced which is greater than the effect of the percarboxylic acid(s); an effect of this type is obtained with a concentration in the range from about 0.1 wt. % to about 10 wt. %.

Use according to the invention of solutions containing one or more percarboxylic acids and the process for applying the same differs from the known use of such solutions for controlling microorganisms and zebra mussels with regard to the objective, namely the control of pathogenic insects and worms. The new use permits pathogenic insects and worms to be controlled in an effective and technically simple manner by killing the larvae. The agent to be used, after the percarboxylic acid has been effective, is rapidly biodegraded so that no ecological problems are to be feared. However, care should be taken when choosing the concentration of percarboxylic acid(s) and hydrogen peroxide in a solution which is to be sprayed onto plants since high concentrations may also be toxic to plants.

The invention is explained by means of the following examples.

EXAMPLE 1

Controlling black mosquito larvae: water, in which 10 larvae were present, was inoculated with 50 ppm of peracetic acid (PAA) by using an equilibrium peracetic acid solution with a concentration of 5 wt. % of PAA and 27 wt. % of hydrogen peroxide. Within 12 hours after inoculation, 5 larvae died; the remaining animals exhibited symptoms which correlated with painful reactions in the gill tubules (doubling up and restless swimming to and fro).

EXAMPLE 2

Water containing 10 black mosquito larvae was inoculated with 50 ppm of peracetic acid using an equilibrium peracetic acid solution with a concentration of 5 wt. % of PAA and 27 wt. % of hydrogen peroxide and also 3 wt. % of Hostapur S30 (30% strength aqueous solution of a mixture of various secondary alkane sulfonates from Hoechst AG). Within 12 hours after inoculation, 6 larvae died. Here again the larvae which did not die demonstrated the symptoms of damage exhibited in example 1.

COMPARATIVE EXAMPLE 1

Water containing the same population of black mosquito larvae as in examples 1 and 2 was inoculated with 1500 ppm of $H_2O_2$ using a 50 wt. % strength hydrogen peroxide solution. None of the larvae died.

EXAMPLE 3

Controlling mayfly larvae: water containing 10 larvae was inoculated with 7 ppm of peracetic acid using an equilibrium peracetic acid with a concentration of 5 wt. % of PAA and 27 wt. % of hydrogen peroxide. All the larvae were dead after 8 hours.

EXAMPLE 4

Controlling red mud worms (tubifecetes): Water, in which the experimental animals were present, was inoculated with 30 ppm of peracetic acid using an equilibrium peracetic acid solution with a concentration of 2 wt. % of PAA and 48 wt. % of hydrogen peroxide. All the animals died.

COMPARATIVE EXAMPLE 2

In the same way as in Example 4, water containing red mud worms was inoculated with 800 ppm of a 50 wt. % hydrogen peroxide solution. None of the experimental animals died.

EXAMPLE 5

A population of red mosquito larvae (chironimides) was inoculated by inoculating with 400 ppm of a 5 wt. % strength equilibrium peracetic acid solution (5 wt. % PAA, 27% $H_2O_2$). All the larvae died within 2 hours.

What is claimed is:

1. A process for controlling and destroying small creatures selected from the group consisting of insects and worms which are pathogenic to humans, animals and plants comprising:

applying or introducing a liquid controlling agent to surfaces or in water, said liquid controlling agent comprising:
an aqueous percarboxylic acid solution comprising one or more percarboxylic acids with 1 to 6 carbon atoms and a mineral acid selected from the group consisting of orthophosphoric acid, pyrophosphoric acid and polyphosphoric acid having the formula $H_{n+2}P_nO_{3n+1}$, wherein n is an integer with a value of at least 3, the mineral acid being present in an amount of 0.1 to 3 wt. %.

2. A process according to claim 1, wherein:

the aqueous percarboxylic acid solution contains at least one member selected from the group consisting of peracetic acid and performic acid.

3. A process according to claim 2, wherein:

the aqueous percarboxylic acid solution contains percarboxylic acid(s), carboxylic acid(s) from which the percarboxylic acid(s) are derived and hydrogen peroxide, or a dilute solution prepared therefrom prior to use.

4. A process according to claim 3, wherein the aqueous percarboxylic acid solution is at or close to equilibrium.

5. A process according to claim 1, wherein:

the percarboxylic acid solution contains 0.1 to 5 moles of percarboxylic acid(s) per liter.

6. A process according to claim 5, wherein the percarboxylic acid solution contains 0.2 to 2 moles of percarboxylic acid(s) per liter.

7. A process according to claim 1, wherein:

the percarboxylic acid solution also contains one or more surfactants.

8. A process according to claim 7, wherein:

the percarboxylic acid solution contains 0.1 to 10 wt. % of surfactants, selected from the group consisting of readily biodegradable anionic and non-ionic surfactants.

9. A process for controlling and destroying small creatures selected from the group consisting of insects and worms which are pathogenic to humans, animals and plants by applying or introducing a liquid controlling agent to surfaces or in water, comprising:

adding an aqueous percarboxylic acid solution containing one or more percarboxylic acids with 1 to 6 carbon atoms as the controlling agent, and spraying the percarboxylic acid solution onto the surface of water which contains insect larvae or introducing the percarboxylic acid solution into the water and distributing it close to the surface, whereby insect larvae are killed.

10. A process according to claim 1, comprising:

spraying the percarboxylic acid solution onto or introducing the percarboxylic acid into a medium which contains the pathogenic small creatures in such an amount that concentration of percarboxylic acid in a preferred habitat of the small creatures is 1 to 5000 ppm.

11. A process according to claim 10, wherein the concentration of percarboxylic acid is 10 to 500 ppm.

12. A process for controlling and destroying small creatures selected from the group consisting of insects and worms which are pathogenic to humans, animals and plants, said process comprising:

applying or introducing a liquid controlling agent to surfaces or in water, said liquid controlling agent including an aqueous percarboxylic acid solution comprising:

(i) peracetic acid and performic acid, and (ii) a mineral acid selected from the group consisting of orthophosphoric acid, pyrophosphoric acid and polyphosphoric acid having the formula $H_{n+2}P_nO_{3n+1}$, wherein n is an integer with a value of at least 3, the mineral acid being present in an amount of 0.1 to 3 wt. %.

13. A process according to claim 12, wherein the performic acid is formed in situ prior to use by mixing a peracetic acid solution and a source of formic acid.

14. A process according to claim 13, wherein the source of formic acid comprises formic acid or a water-soluble formate.

15. A process according to claim 12, wherein the aqueous percarboxylic acid solution comprises percarboxylic acids, carboxylic acids from which the percarboxylic acids are derived and hydrogen peroxide, or a dilute solution prepared therefrom prior to use.

16. A process according to claim 15, wherein the aqueous percarboxylic acid solution is at or close to equilibrium.

17. A process according to claim 12, wherein the percarboxylic acid solution contains 0.1 to 5 moles of percarboxylic acids per liter.

18. A process according to claim 17, wherein the percarboxylic acid solution contains 0.2 to 2 moles of percarboxylic acids per liter.

19. A process according to claim 12, wherein the percarboxylic acid solution also contains one or more surfactants.

20. A process according to claim 19, wherein the percarboxylic acid solution contains 0.1 to 10 wt. % of surfactants selected from the group consisting of readily biodegradable anionic and non-ionic surfactants.

21. A process according to claim 12 further comprising spraying the percarboxylic acid solution onto the surface of water which contains insect larvae or introducing the percarboxylic acid into the water and distributing it close to the surface, thereby killing insect larvae.

22. A process according to claim 12, comprising spraying the percarboxylic acid solution onto or introducing the percarboxylic acid into a medium which contains pathogenic small creatures in such an amount to establish a concentration of percarboxylic acid in a preferred habitat of the small creatures of 1 to 5000 ppm.

23. A process according to claim 22, wherein the concentration of percarboxylic acid is 10 to 500 ppm.

* * * * *